United States Patent [19]

Scioppacassi

[11] Patent Number: 4,772,588
[45] Date of Patent: Sep. 20, 1988

[54] TREATMENT OF PARASITIC DISEASES WITH CALF THYMUS EXTRACT

[75] Inventor: Giovanna Scioppacassi, Milan, Italy

[73] Assignee: Istituto Farmacologico Serono S.p.A., Italy

[21] Appl. No.: 857,116

[22] Filed: Apr. 29, 1986

[30] Foreign Application Priority Data

May 3, 1985 [IT] Italy .................. 48029 A85

[51] Int. Cl.⁴ .............................. A61K 35/26
[52] U.S. Cl. ........................ 514/21; 424/95; 424/101; 514/2; 514/8; 530/397; 530/399
[58] Field of Search ............ 424/95, 101; 514/2, 514/8, 21; 530/397, 399

[56] References Cited

U.S. PATENT DOCUMENTS

| | | | |
|---|---|---|---|
| 4,010,148 | 3/1977 | Goldstein | 530/399 |
| 4,128,637 | 12/1978 | Naylor et al. | 514/21 X |
| 4,133,804 | 1/1979 | Bach et al. | 530/399 X |
| 4,239,498 | 12/1980 | Rule | 424/95 X |
| 4,250,084 | 2/1981 | Trainin | 424/95 X |
| 4,521,407 | 6/1985 | Pelham et al. | 424/95 |
| 4,571,336 | 2/1986 | Houck et al. | 424/95 |
| 4,576,696 | 3/1986 | Oertli | 424/95 X |

OTHER PUBLICATIONS

Chem. Abstracts, 94 (1981), 81996v, Falchetti et al. Abstracts of 1976 3rd European Immunology Meeting on Aug. 25-27, 1976.
Falchetti et al., "Pharmacological and Biological Properties of a Calf Thymus Extract (TP-1)", Drugs Exptl. Clin. Res. 3 (2) 39-47 (1977).
Bergesi et al., "Chemical Characterization and Biological Activity of a New Thymic Extract", Folia Aleergol Immunol. Clin. 21:201, 1977.
Falchetti et al., "Bioassay for Thymic Extracts: Guinea Pig Spleen Lymphocytes-Rabbit Red Blood Cells Rosette Method", Cancer Biochem. Biophys., 1979, vol. 4, pp. 69-74.

*Primary Examiner*—Howard E. Schain
*Attorney, Agent, or Firm*—Ostrolenk, Faber, Gerb & Soffen

[57] ABSTRACT

A course of a parasitic, e.g. protozoal, infection is combated by administering to the host an immunomodulating effective amount of a calf thymus hormone extract.

5 Claims, No Drawings

TREATMENT OF PARASITIC DISEASES WITH CALF THYMUS EXTRACT

Parasitic infections, chiefly malaria but also leishmaniasis, trypanosomiasis, amoebiasis, etc., constitute the most important causes of disease and mortality in the world. Research in this field is of primary interest not only for endemic, mostly tropical Countries but also for other areas in which some formerly indigenous infections are presently extinct or greatly reduced in incidence, but are steadily imported by travellers from other lands.

The attempt for the control of parasitic diseases can be divided into four main groups. These are (a) the attempt to completely eradicate the infection; (b) the containment of the drug resistance phenomenon which is so easily displayed by parasites; (c) the discovery and introduction into the therapeutic armamentarium of new, more active drugs; and (d) the activation of the resources of the main antagonist of any agent, that is, the reaction of the host.

The optimal solution of the problem is, of course, represented by the eradication of the parasite but the achievement of this goal takes time, measurable in terms of centuries, and would appear also to require revolutionary changes in environmental and socio-economic conditions of populations dwelling in very large areas. The possibility of establishing a policy of chemotherapeutic prevention and treatment capable of not creating treatment-resistant mutants appears equally remote. The intrinsic variability of the parasitic species and the impossibility of controlling the incongruous application of chemotherapeutic drugs precludes the way to any fruitful attempt to avoid the problems of drug resistance. One of the most impressive examples of the difficulties of this approach is the unremitting broadening of areas occupied by multiple drug-resistant strains of *P. falciparum*. The prospects of obtaining new drugs for the treatment of parasitic infection is not very hopeful.

The search for new anti-parasitic compounds appears to be at a fairly low level, especially when compared with other fields of chemotherapy, in spite of the efforts of the World Health Organization's special programmes and the recommendations of a few commentators.

Against this background, the perspective of an immunotherapeutic or prophylactic approach takes on special relevance.

While immunology is a well-established branch of the biomedical sciences, immunoparasitology is a very new field which has only begun to produce experimental and clinical data over the last few years.

When challenged by the penetration of a parasite, the host can either unconditionally surrender or engage itself in the struggle by mounting a complex immune reaction that eventually results in either sterile or modulating or concomitant immunity. Sterile immunity is evidenced by the elimination of the parasite with a residual (sometimes long lasting) resistance toward subsequent infections.

A modulating immunity occurs when a complete and efficient immune reaction is raised by the host against the antigenic structure(s) of the parasite and succeeds in destroying the majority of the infecting population.

A number of parasites, however, are capable of evading host reactions through various mechanisms, for instance, the capacity to express different antigenic determinants. The multiplication of such a resistant population brings about a new parasitic wave and the mounting of a new host reaction which follows the steps of the previous reaction in a continuing cycle. It follows that the characteristics of the parasitic population are continuously modulated by the host reaction. The natural history of disease is deeply influenced by these phenomena. A prime example is given by the recurrent course of the parasitemia in the African trypanosomiasis. In this case, the parasites eventually invade the central nervous system and multiply, finding the central nervous system a sanctuary which provides suitable protection against the attack of the iterative immune reaction.

The case of the concomitant immunity is quite different. Here, the immune reaction elicited by the parasite is unable to eradicate the infection and persists as long as the parasite itself remains within the host. From a teleological point of view, this condition appears to be the most advantageous one for both partners. An efficient concomitant immunity reaction on one side decreases the host "permissivity" toward the otherwise hardly tolerable superinfections and on the other side slows down parasitic growth, but ensures the first arrived parasitic population a fair probability of being the last one to be expelled, providing expulsion ever occurs.

From an operational point of view, three main groups of immune reactions can be identified. These are "prohost reactions" which are aimed at either the restriction of parasite proliferation or the prevention of parasite-associated reactions that jeopardize the host's biologic equilibrium, "pro-parasite reactions" which act in favor of the parasite infection, and the so called "inconsequential reactions" which are presumed to be the void of a direct and immediate effect on the host-parasite relationship.

From a mechanical point of view, the above-mentioned phenomenon can be interpreted as the effect of a disarray of immunocytic population functions selectively induced by direct or indirect parasitic actions. Many different mechanisms cna be operating. Some parasites are capable of evading the reaction of the immunocytes by invading them, exemplified by the ability of *Theileria parva* to preferentially colonize a subpopulation of lymphocytes and of Leishmania to grow in macrophages. Perhaps more relevant is the influence exerted by parasites on immunocytes through long-range mediators, i.e. soluble factors. A good example is the polyclonal activation of B cells which hinder the efficient production of specific antibodies toward parasite-related and unrelated antigens through a wide expression of the B cell repertoire and the flooding with an array of useless or autoimmune antibodies. Through a feed back mechanism, polyclonal B cell activation also induces stimulation of suppressor cells and this sometimes inane attempt of the immune system to break down a process severely impairing the humoral response results in a long-standing activation of suppressors which act to sustain a generalized immunosuppression.

Various information points toward the role played by the suppression phenomena in the pathogenesis of parasitic diseases. Thus, spleen macrophages of malaria-infected mice are capable of inhibiting the normal spleen cell response to PHA an LPS. Activated macrophages are presented not only in the spleen, but also in the liver of these animals and their function is altered, but their antigen-presenting capacity does not seem to be impaired. Several other facts concur in sustaining the severe derangement of cellular and humoral immune response occurring in these infections, such as the parasite-induced synthesis of anti-N and anti-T autoantibodies and the production by the parasite of suppressor substances, not only in culture, but also in the host's blood.

The pivotal part played by T-lymphocyte and cell mediated immunity in experimental or human malaria has been emphasized but some problems, e.g. the role of Nk cell and their mediators, are still controversial.

There have been previously reported observations on the thymus dependancy of a number of symptoms occurring in plasmodial infections such as splenomegaly, anemia, and enhanced phagocytosis, and the altered course of the disease in athymic or thymectomized animals. Also in animal models of leishmaniasis, the importance of the role of cellular immunity is supported by experimental findings. (Coutinho et al,. Induction by Specific T Lymphocytes of Intracellullar Destruction of *Leishmania major* in Infected Murine Macrophages, Paras. Immunol. 6, 157-170 (1984)). Specific T-cell clones are capable of mediating helper activity, DTH response and macrophage activation (Louis et al, The In Vitro Generation and Functional Analysis of Murine T Cell Populations and Clones Specific for a Protozoan Parasite: *Leishmania tropica*, Immunol. Rev. 61, 215-240 (1982)) that represent the prominent mechanisms responsible for the elimination of leishmania (Manuel et al, Leishmaniais: Immunity, Immunopathology and Immunodiagnosis, in Immunology of Parasitic Infections (Cohen and Warren, Eds., p. 299, Blackwell Scientific Publications, Oxford 1982)).

While the foregoing considerations would seem to indicate the use of immunomodulators in treating parasitic diseases, as will be shown below, it has been found that immunomodulators cannot be considered as a group of interchangeable and constantly salutary substances. Congruous evidence is also provided by clinical trials with dexamethasone, a substance endowed with strong lymphocytolitic and immunomodulating properties. The use of the steroid in the treatment of human cerebral malaria is, however, deleterious. (Warrell et al, Dexamethasone Proves Deleterious in Cerebral Malaria: A Double Blind Trial in 100 Comatose Patients, New Eng. J. Med., 306, 313-319 (1982)).

A study of the activity of cyclophosphamide (hereinafter termed "CPA") and TP-1 (described further below) on murine plasmodial infections was carried out. Both CPA and TP-1 are immunomodulating substances endowed with a direct activity on T-cell and thymus function and devoid of direct antiparasitic activity.

*Plasmodium berghei*, maintained by intraperitoneal inoculation of 105 parasitized red blood cells (PRBC) in outbred mice was employed. Groups of 20 female CD1 Cobs mice (Charles River) weighing 18-20 grams were infected by the intraperitoneal route with 104 (schemes 1 and 2) or 106 (scheme 3) P-RBC/mouse and deaths were recorded for the following 25 days. Commercially available CPA and TP-1 were dissolved in sterile saline. In the treatment schemes, reported in the tables, 10 mg/Kg s.c. of TP-1 and 200 mg/Kg i.p. CPA were administered. Scheme 3 was the same as scheme 2 except that the low dose of merogenic units of *P. berghei* (chronic course) was changed to the high dose (acute course). The results are set forth in the following Tables 1-3.

TABLE 1

Scheme 1

| Material | Day Administered | % Survival at Day 14 |
|---|---|---|
| CPA | −1 | 40 |
| CPA + TP-1 | −1 −3,−2 | 65 |
| TP-1 | −3,−2 | 100 |
| Saline | −3,−2,−1 | 50 |

| | Median Days to N % Mortality | | |
|---|---|---|---|
| | 10% | 50% | 90% |
| CPA | 6 | 12 | 17.5 |
| CPA + TP-1 | 10 | 14.5 | 18 |
| TP-1 | 15 | 25 | 25 |
| Saline | 9 | 13.5 | 19 |

TABLE 2

Scheme 2

| Material | Day Administered | % Survival at Day 14 |
|---|---|---|
| CPA | −1 | 35 |
| CPA+ TP-1 | −1 +1,+2,+3 | 60 |
| Saline | −1,+1,+2,+3 | 45 |

| | Median Days to N % Mortality | | |
|---|---|---|---|
| | 10% | 50% | 90% |
| CPA | 4.5 | 10 | 15.2 |
| CPA + TP-1 | 9 | 16 | 21 |
| Saline | 8 | 12 | 16 |

TABLE 3

Scheme 3

| Material | % Survival at Day 14 |
|---|---|
| CPA | 45 |
| CPA + TP-1 | 70 |
| Saline | 20 |

| | Median Days to N % Mortality | | |
|---|---|---|---|
| | 10% | 50% | 90% |
| CPA | 9 | 13 | 24 |
| CPA + TP-1 | 10.5 | 19 | 25 |
| Saline | 6.5 | 7.5 | 22.5 |

Anatomohystological examination confirmed the predominance of the lymphocytic component in the inflammatory response. In infected animals, the overwhelming majority of cells infiltrating the various organs, chiefly the liver, present the morphologic characteristics of activated lymphocytes, predominantly endowed with markers of T lineage, but also including a number of plasma cells. In the spleen, besides the typical structural derangements and, particularly in the case of the more slowly evolving disease, a dramatic increase in the number of megakaryocytes can also be easily detected.

The survival results demonstrate that the course of the infection takes a significantly different shape in the treated animals as compared with the control animals.

When the infection takes a slow, sub-acute course, the administration of CPA one day before (or one day after) the inoculation of plasmodia exerts a pro-infectious activity. Contrarily, a pro-host effect is observed when the same treatment is carried out in animals infected with a greater number of merogenic units and the disease takes a rapidly lethal course.

The behaviour of TP-1 is quite different. Its administration consistently displays a pro-host effect that can be synergistic with the pro-host effect of CPA or antagonistic to the pro-parasitic action of CPA. The anti-infectious effect of TP-1 is present when the preparation is administered either before or after the injection of parasite. The activity of TP-1, contrary to the activity of CPA, does not depend on the characteristics of the course of the disease. Of course, any treatment based on the synergistic action of CPA and TP-1 must be carefully designed to take into account the known toxicity of CPA. TP-1 is a known calf thymus extract which has been described, inter alia, in Falchetti, et al., "Isolation, Partial Characterization and Biological Effects of a Calf Thymus Factor". Abstracts of Third European Immunology Meeting, Copenhagen, Aug. 25-27, 1976; Falchetti, et.al, "Pharmacological and Biological Properties of a Calf Thymus Extract (TP-1)", Drugs Exptl. Clin. Res. 3 (2) 39-47 (1977)); Bergesi, et al., "Chemical Characterization and Biological Activity of a New Thymic Extract", Folia Allergol. Immunol. Clin. 21: 201, (1977); and Falchetti, et al., "Bioassay for Thymic Extracts: Guinea Pig Spleen Lymphocytes-Rapid Red Blood Cells Rosette Method", Cancer Biochem. Biophys. Vol. 4, pp. 69-74 (1979)

The extraction and purification of TP-1 is described in the Bergesi, et al. article as follows: homogenized calf thymuses were extracted with ammonium acetate 0.15 M. and centrifuged in the presence of decalcite. the liquid thus obtained was collected and heated at 70 C for 30 minutes.

The proteins coagulated using this procedure were separated by filtration and the clear liquid was precipitated by addition of ammonium sulphate until a 45% saturation had been achieved. The clear liquid obtained after separation of the precipitate via centrifugation, was brought to 90% saturation with ammonium sulphate. The precipitate from this last pass was collected by filtration, dissolved in water and ultrafiltered across a PM-10 membrane. The ultrafiltrate containing salts and protein matter with a molecular weight lower than approximately 10,000 was then lyophilized, desalted on Sephadex G-25 and subsequently gel-filtered on Sephadex G-50. Collected were the fractions which, on electrophoresis in polyacrylamide gel at pH 8.6, showed two characteristic bands with an Rf of about 0.25 and 0.44 compared with bromophenol blue used as a tracer.

TP-1 has been found to have the capacity to increase the responsiveness of mouse spleen lymphoid cells to phytohaemoagglutinin (PHA) and to concanavalin A stimulation, while it did not increase the response to lipopolysaccharide stimulation; to stimulate an increase in E-rosette forming lymphocytes from human cord blood, to increase the percentage of Theta-positive cells of the mouse spleen population and to stimulate the capacity of allogeneic mouse marrow cells to induce a graft v. host response in X-ray irradiated mice. TP-1 did not cause any acute toxic effect or noticeable side effects in doses of up to 100 mg./Kg. when administered intraperitoneally to mice for 21 days or to rats for 31 days, nor when administered subcutaneously to rats for 180 days in doses up to 50 mg./Kg., nor in dogs receiving intramuscular doses up to 10 mg./Kg. for 180 days. It did not alter the neuromuscular transmission as evaluated in vitro on the rat phrenic diaphragm nerve and in vivo on the mouse tibial muscle, nor the blood pressure or the electrocardiographic and pneumographic pattern.

TP-1 can easily be differentiated from other thymic extracts because it has two main characteristic bands upon electrophoresis on a polyacrylamide gel at pH 8.6 while other thymic extracts presently known show only a single characteristic band. At pH 8.6, TP-1's two bands are at $Rf=0.25\pm0.05$ and $Rf=0.45\pm0.05$.

To date, TP-1 has been administered principally by intramuscular injection although other modes of administration can also be employed. The pharmaceutical preparations contain an anti-parasitic infection effective amount of TP-1 together with a compatible, pharmaceutically acceptable carrier or diluent which, in case of the intramuscular formulation, may be sterile water.

Other conventionally employed excipients such as mannitol can also be included, and the usual array of excipients can be employed in other administration forms.

The anti-parasitic (e.g. antiplasmodial) effective amount of TP-1 is dependent on the age and weight of the individual being treated, the mode of administration and the presence or absence of other infections or diseases. While the dosage administered per day can typically be in the range of about 0.5 to about 1.0 mg./Kg., the response varies considerably from individual to individual and is therefore best determined by the attending clinician.

Various changes and modifications can be made in the process of this invention without departing from the spirit and scope thereof. The various embodiments which are set forth herein are for the purpose of further illustrating the invention and are not intended to limit it.

We claim:

1. A method of treating a parasitic infection in a mammal which is characterized by the administration of an anti-parasitic infection effective amount of a calf thymus extract, which extract is devoid of direct antiparasitic activity and shows, upon electrophoresis on polyacrylamide gel at pH 8.6, two main characteristic bands with an Rf about 0.25 and 0.44.

2. The method of claim 1, further characterized in that the calf thymus extract is administered parenterally.

3. The method of claim 2, further characterized in that the calf thymus is administered intramuscularly.

4. The method of any of the preceeding claims further characterized in that the amount of calf thymus extract administered per day is in the range of about 0.5 to about 1.0 mg./Kg.

5. The method of claim 1, further characterized in that the infection is plasmodial and an antiplasmodial effective amount is administered.

* * * * *